United States Patent [19]
Lee

[11] Patent Number: 5,669,771
[45] Date of Patent: Sep. 23, 1997

[54] DENTAL RESTORATION HOLDER SYSTEM

[76] Inventor: Robert L. Lee, 22937 Grand Terrace Rd., Grand Terrace, Calif. 92324

[21] Appl. No.: 370,187

[22] Filed: Jan. 9, 1995

Related U.S. Application Data

[63] Continuation-in-part of Ser. No. 220,115, Mar. 30, 1994, Pat. No. 5,575,649, which is a continuation-in-part of Ser. No. 196,420, Feb. 15, 1994, Pat. No. 5,525,059, which is a continuation-in-part of Ser. No. 836,065, Feb. 12, 1992, Pat. No. 5,320,533.

[51] Int. Cl.$^6$ .................................................. A61C 5/08
[52] U.S. Cl. ................................................. 433/218; 433/215
[58] Field of Search .................................. 435/141, 218, 435/70, 71, 146, 147, 214, 215, 152, 153, 157, 156, 162, 163; 223; 294/1.2, 19.1, 1.1, 25

[56] References Cited

U.S. PATENT DOCUMENTS

| | | |
|---|---|---|
| 939,476 | 11/1909 | Copp . |
| 1,106,815 | 8/1914 | Hopkins . |
| 1,202,698 | 10/1916 | Ford . |
| 1,809,423 | 6/1931 | Peck . |
| 1,990,381 | 2/1935 | Ivory . |
| 2,567,794 | 9/1951 | Winett . |
| 3,285,409 | 11/1966 | Loran . |
| 3,468,031 | 9/1969 | Mumaw . |
| 3,628,249 | 12/1971 | Wurl . |
| 3,748,741 | 7/1973 | Yerkes, Jr. . |
| 3,903,605 | 9/1975 | Malmin . |
| 3,919,775 | 11/1975 | Malmin . |
| 3,974,567 | 8/1976 | Ridgeway . |
| 4,073,530 | 2/1978 | Seidler . |
| 4,185,384 | 1/1980 | Lustig et al. . |
| 4,219,619 | 8/1980 | Zarow . |
| 4,265,618 | 5/1981 | Herskovitz et al. . |
| 4,293,074 | 10/1981 | Dunsky . |
| 4,382,784 | 5/1983 | Freller . |
| 4,410,209 | 10/1983 | Trapani . |
| 4,486,177 | 12/1984 | Lekawa . |
| 4,604,059 | 8/1986 | Klaus et al. ............... 433/218 X |
| 4,664,628 | 5/1987 | Totaro . |
| 4,725,233 | 2/1988 | Planert . |
| 4,773,857 | 9/1988 | Herrin . |
| 4,834,654 | 5/1989 | Nussbaum . |
| 4,919,615 | 4/1990 | Croll . |
| 4,953,902 | 9/1990 | Brown . |
| 4,975,053 | 12/1990 | Hofsess . |
| 4,993,949 | 2/1991 | Hill . |
| 5,035,615 | 7/1991 | Din . |
| 5,040,981 | 8/1991 | Oliva . |
| 5,098,292 | 3/1992 | Lazarof . |
| 5,197,877 | 3/1993 | Andrews . |
| 5,197,878 | 3/1993 | Lukase et al. . |
| 5,256,064 | 10/1993 | Riihimaki et al. . |

FOREIGN PATENT DOCUMENTS 4027955  12/1991  Germany .

OTHER PUBLICATIONS

Photocopy of "Pic-n-Stic" device manufactured by Pulpdent Corp., 1990.

Primary Examiner—Nicholas D. Lucchesi
Attorney, Agent, or Firm—Knobbe, Martens, Olson & Bear, LLP

[57] ABSTRACT

A small, thin, flat, stiff tab is glued with a hot melt adhesive to the exterior surface of a dental restoration. For veneers, a primer is applied to the veneer before the adhesive to enhance the bond. The tab can then be gripped between a thumb and forefinger while placing the restoration on a tooth to which it is to be laminated. After the restoration is placed on the tooth with permanent bonding material between the restoration and the tooth, the tab is used as a vibrating transmitter to the restoration. The tab is vibrated by positioning a flat-sided dental shaft against the tab or an extension element and rotating the shaft with a dental handpiece. A group of tabs are conveniently supported in slots formed in the upper surface of a support. The slots are dimensioned in relation to the tabs in a manner such that one end of a tab is in a slot while the finger gripping area of the tab extends upwardly, away from the support for convenient gripping by a person's fingers. After the tab is attached to a restoration, it may be inserted and returned to a slot in a holder.

12 Claims, 4 Drawing Sheets

DENTAL RESTORATION HOLDER SYSTEM

CROSS-REFERENCE TO RELATED APPLICATION

This application is a continuation-in-part of U.S. patent application Ser. No. 08/220,115, filed Mar. 30, 1994, now U.S. Pat. No. 5,575,649 which is a continuation-in-part of U.S. Pat. application Ser. No. 08/196,420, filed Feb. 15, 1994, now U.S. Pat. No. 5,525,059 which is a continuation-in-part of U.S. patent application Ser. No. 07/836,065 filed Feb. 12, 1992, now, U.S. Pat. No. 5,320,533, issued Jun. 14, 1994.

FIELD OF THE INVENTION

The present invention relates generally to dental techniques and equipment, and more specifically to a system for facilitating the positioning of tooth veneers or other dental restorations on patient's teeth and the handling of such restorations in the laboratory.

BACKGROUND OF THE INVENTION

For a variety of reasons, the enamel surfaces of teeth sometimes become permanently stained, decayed or damaged. A technique has been developed to repair or improve the appearance and function of such teeth.

In a procedure referred to as cosmetic bonding, a thin veneer of ceramic or plastic having a shape and curvature matching the outline, shape and surface curvature of a tooth to be refaced is bonded to the facial or labial surface of the tooth, after the tooth has been specially prepared. The veneer has a desired surface coloration and gloss to match adjacent teeth. The veneer is sufficiently opaque to mask a stained surface of the underlying tooth. By this procedure, teeth may be restored to a more pleasing and functional appearance.

Cosmetic bonding includes a sequence of steps requiring exercise of a substantial degree of artistic craftsmanship. The dentist must prepare each tooth to receive a veneer and make accurate impressions of the prepared teeth. Teeth impressions are made by forming a dental impression material over the teeth and allowing the material to harden. Impressions are then used by a dental ceramist or a dentist to make a veneer. In one procedure the impressions are used to make molds in which the required ceramic veneers are eventually fabricated. Each veneer is individually fabricated and must have the desired precise dimensions, coloration, luster, and opacity.

The number of individually demanding steps required to fabricate each tooth veneer results in a substantial investment in time. Thus, the replacement value of each custom-made veneer is significant. Accordingly, considerable care must be exercised in handling a veneer to avoid damage to it. The veneer is relatively fragile until it has been bonded or laminated to and supported by the tooth for which it was custom-fabricated.

After a number of preparation steps, the veneer is temporarily placed on the appropriate tooth. The purpose of the temporary placement is to check size, opacity and coloration of the veneer. After this preliminary testing, the veneer is removed, and both the veneer and tooth thoroughly cleaned of the temporary adhesive and dried. The veneer or other restoration is then permanently bonded to the supporting tooth. Typically this is done with a light sensitive bonding agent. The inner surface of the restoration is coated with such bonding agent, and the restoration placed in position on the tooth. All of these procedures are usually performed by the dentist holding the substantially small, fragile restoration between his or her thumb and forefinger. Needless to say, many of these small restorations are inadvertently dropped or damaged during the fitting, adjustment and placement phase.

Another difficulty encountered in positioning and permanently bonding a restoration to a tooth concerns the permanent bonding agent employed. One type that is frequently utilized is a composite resin that is fairly viscous or stiff. The material should, of course, be spread between all of the mating surfaces of the restoration and the base tooth. It is also desirable that any excess bonding agent be squeezed out from between the restoration and the tooth. In one current attempt at accomplishing this, the dentist will press a finger on the restoration and roll the finger from side to side, while balancing the force with a finger on the backside of the tooth. This is not a very effective method. Dental crowns are sometimes seated using a vibrating pad clamped between the crown and the mating tooth and the opposing jaw. This method cannot be used with a veneer since there is no mating biting surface.

After the bonding agent spreading step is completed, the bonding agent is cured. Typically this is accomplished by irradiating the outer surface of the restoration with a small intense light source. Light transmitted through the restoration produces a photo-chemical reaction in the bonding agent, causing it to harden.

During the light exposure process, which takes between 20 and 60 seconds, the dentist must hold the restoration in a precisely aligned position with respect to the tooth. If the restoration is displaced from its aligned position during the bonding process, the restoration may have to be ground off the tooth, and a replacement restoration fabricated.

Because of the difficulty of handling and positioning the restoration, a variety of tools and techniques have been developed. These prior systems have various disadvantages such as complexity, difficulty in using or ineffectiveness. Thus, it is believed that many restorations are positioned only with fingers. Accordingly, a need exists for an improved, simplified tool and technique for handling veneers and other restorations. There is also a need for improving the means for spreading the bonding agent that joins the restoration to the underlying tooth.

SUMMARY OF THE INVENTION

Briefly stated, a small, relatively flat, thin, stiff element forms a tab-like holder for manipulating and positioning a tooth restoration such as a veneer, crown or inlay. One edge of the planar element is attached to the outer surface of the restoration with an adhesive which provides a firm attachment that is sufficiently strong when solidified to hold the element in an edge-wise position with respect to the restoration. That is, the element extends generally perpendicular to the restoration outer surface to form a tab attached to the restoration. This enables the restoration to be positioned and manipulated by simply gripping the tab between the thumb and a finger of one hand. With that arrangement, the thumb and finger are engaging or are close to the restoration, which greatly facilitates control and positioning of the restoration on the patient's tooth.

Since the exterior surface of a tooth veneer is quite smooth and flat it is preferable that a primer coating first be applied to the exterior surface of the veneer before hot melted adhesive is applied. The purpose of the primer coating is to improve the bond between the veneer and the edge of the tab to be attached to the veneer. One suitable primer material is normally transparent; and hence to enable the operator to make certain that the primer is applied over the entire area to be covered by the adhesive, it is desirable that a suitable pigment be added to the primer such that the coating applied to the veneer can be easily seen. This primer may, of course, be used on other types of restorations such as crowns and inlays.

In the preferred form of the invention, the adhesive employed is solid at room temperature, although slightly resilient, but becomes flowable when heated. A preferred example of that is a hot-melt adhesive, which can be conveniently heated by and dispensed from a glue gun. Preferably, a quantity of heated glue is applied to the restoration and to an edge of the tab, and the two are then joined in a desired position. In use with a tooth veneer, the planar tab is desirably oriented either vertically or horizontally with respect to the long axis of the veneer, as it would be placed on the tooth.

The tab may be made of various materials, but is preferably made of a plastic, such as nylon. Further, the tab in one arrangement has a pair of spaced edge points on the edge to be attached to the restoration. This creates a recessed area in the edge portion between these points. An advantage of this arrangement is that the two points form an attachment base with flat or curved restoration surfaces. Also, the adhesive can surround the two points and fit within the recess as well. Also, there may be provided a small hole in each of the points that fills with adhesive. This enables a small quantity of adhesive around that edge of the tab to bond the tab to the restoration in the desired position. Preferably, a hole is also formed in the finger-gripping area of the tab to facilitate the gripping action. This same hole may be conveniently used for attaching a string or floss for purposes of retrieving the restoration and the tab from the patient's mouth in the event the tab is dropped.

The hole in the finger gripping area of the tab also serves an additional function in connection with proper bonding of the restoration to the tooth. After the permanent bonding agent has been applied to the restoration and the restoration has been positioned on the tooth, utilizing the tab, and before curing the bonding agent, a vibrating tool may be inserted into the opening in the finger gripping area of the tab and pressed against the edge of the hole closest to the restoration. Alternatively, the tool can be placed against the edge of the tab remote from the edge secured to the restoration. This causes vibration to be transmitted from the tab to the restoration and thus to the bonding agent. This action causes the bonding agent between the restoration and the tooth to be evenly distributed and causes excess bonding agent to be extruded out around the edges of the restoration. The vibrating tool may be in the form of a shaft having a flat-sided cross-section, with the shaft being rotated by a dental hand piece, and the side of the tool being placed against the tab edge.

Since the tab attached to the restoration is quite small, a vibration transfer tool is useful to allow more finger space. The tool is in the form of a flat stiff element that enables the vibrator to be spaced further from the tab. One end of the element is engaged by the vibrator, and the other end is adapted to fit over an end of the tab in a manner to transmit the vibration of the tool.

After the vibration step, a curing light is applied to the veneer to cure the bonding agent between the veneer and the tooth. When that operation is complete, a small dental knife can be used to cut the adhesive under the tab and separate the tab from the veneer so that the tab, together with that adhesive, may be removed from the veneer and discarded. Isopropyl alcohol on a cotton pellet or a rotary tooth cleaning cup is used to remove residual primer from the face of the veneer.

As another feature of the invention, there is provided a support for conveniently positioning a group of tabs. The lower end of each tab fits within a slot in the upper wall of the support, with the finger gripping area on each tab extending upwardly. With that arrangement, the dentist may conveniently grip the tab with the thumb and forefinger from above in exactly the orientation that is desired when the tab is to be attached to the dental restoration and the restoration is to be positioned on the patient's tooth or on a tooth model in the laboratory. The support is relatively short so that the middle finger or ring finger of the gripping hand may engage a surface on which the support is positioned, so as to stabilize the hand when a tab is being gripped with the thumb and forefinger.

As a further feature of the invention, the slots in the tab support are formed so that the end of the tab which is gripped by the operator's fingers will fit into the slot. Thus, in use, a series of tabs are first positioned with the veneer engaging end of each tab in the slots. After the tab has been gripped, removed, and attached to a veneer, the opposite end of the tab may be conveniently replaced in a slot of the holder with the internal surface of the veneer facing upwardly. The tab with the attached veneer may be conveniently removed and replaced from the holder as many times as is necessary during the fitting and attaching of the veneer to the tooth. The bonding agent for attaching the veneer to the tooth may be applied to the veneer while it is positioned in the holder. A cover positioned over the holder prevents light from curing the bonding agent until the veneer is positioned on the tooth.

DETAILED DESCRIPTION OF THE INVENTION

Figure 1:
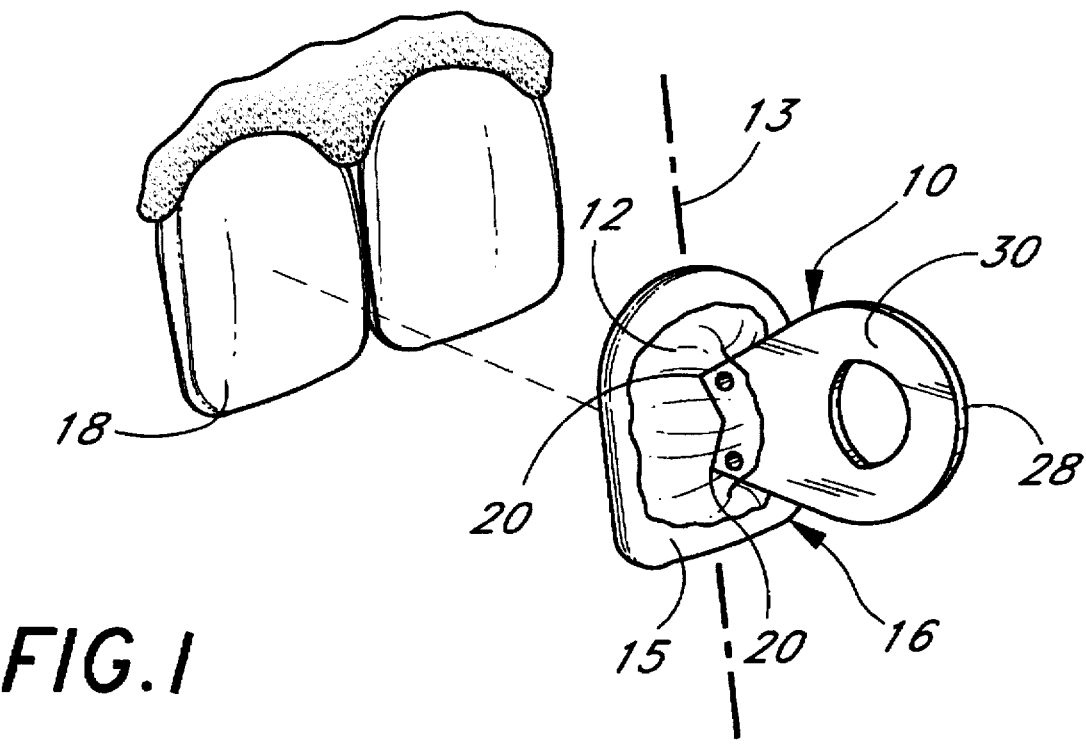
FIG. 1 is an enlarged perspective view illustrating the placement tab of the invention joined to the outer surface of a tooth veneer.

FIG. 1 illustrates a holder placement tab 10 attached by adhesive 12 to the outer surface 15 of a dental restoration in the form of a ceramic veneer 16. The tab is expected to be most useful for positioning a veneer as shown but it can of course be used for crowns and inlays or other dental restorations, either in the mouth or on a laboratory model.

Figure 2:
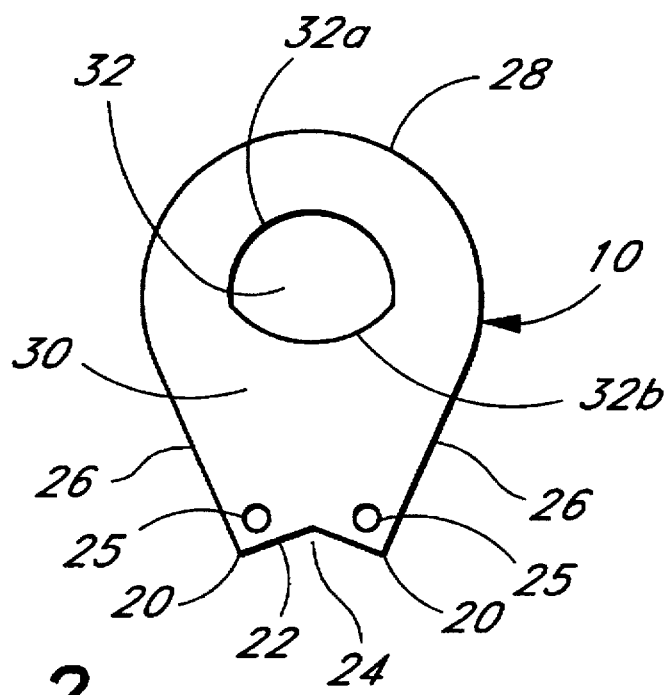
FIG. 2 is a plan view of the pad of FIG. 1.

The tab 10 is in the form of a thin, relatively flat, stiff element which is preferably made of plastic or nylon. Of course, the tab can be made of other materials such as cardboard, wood, or metal. Referring to the plan view of FIG. 2, it may be seen that the tab has a lower or leading edge 22 to engage the veneer. This edge 22 is defined by a pair of spaced end points 20 which are joined by a shallow V-shaped portion that defines a shallow recess 24. In a preferred form of the invention, the angle of the V-shaped recess is about 138°. A small hole 25 is formed near each of the points 20 to receive adhesive used to connect the tab to the veneer.

The tab 10 further has side edges 26 which diverge slightly from the points 20 to a maximum width and merge into a semi-circular upper edge 28. The portion of the tab which is not covered by the adhesive 12 in FIG. 1 forms a finger-gripping area 30. More specifically, there is an area gripped by a thumb and one finger of a person's hand, usually the forefinger, as seen in FIG. 3.

To facilitate gripping the tab, there is formed an opening 32 in the finger gripping area having upper end lower curved edges 32a and 32b which give the hole somewhat of a lemon shape.

An important feature of the invention is that the lower end of the tab has to mate with veneers or other dental restorations having various curvatures. Regardless of the curvature, the two points 20 will engage the veneer surface, thus providing a good base for connection to the veneer. Also, the recess 24 forms a pocket for receiving adhesive and helps adequately attach the tab to the veneer. The points 20 are spaced to accommodate most veneers. The preferred spacing is about 4 mm. Such dimension will allow the tab points 20 to make contact with very small veneers. Of course other dimensions may be employed.

Figure 3:
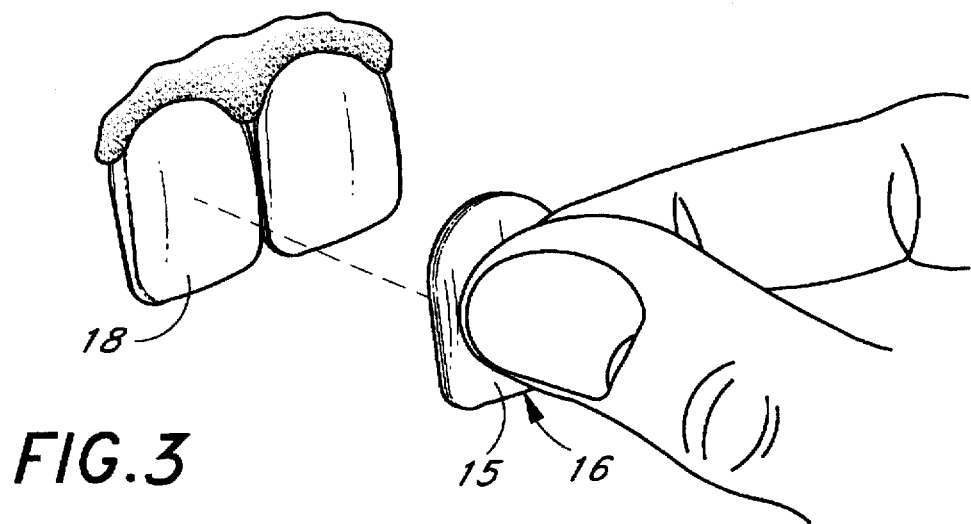
FIG. 3 shows the tab transmitting vibration to the veneer.

One of the other features of the invention is that the tab is to be gripped immediately adjacent to the veneer so as to provide good control in the positioning of the veneer on a tooth 18, as shown in FIG. 3. For that reason and for ease of handling, it is desirable that the tab be no larger than necessary to enable it to be conveniently gripped between the thumb and forefinger of a person's hand. This may be referred to as gripped by "the fingers". The illustration is from the perspective of a viewer in front of the patient. The view from the dentist's perspective would probably be inverted since the dentist is usually positioned behind and above the patient.

In a preferred embodiment of the tab, the width of the tab at its widest, where the side edges 26 merge with the upper edge 28, is a little under 10 mm, and the distance from the points 20 and a tangent through the center of the upper edge 28 of the tab is only about 13 mm. Thus the tab is about the size of a penny or smaller, preferably only about the size of a small fingernail. These dimensions can be somewhat larger, but the tab flat side should be no greater than one inch in any direction, in that it then becomes cumbersome to use. The tab planar dimensions are much greater than its thickness, preferably only about 0.030 inches (0.8 mm) thick.

It is desirable that the hole 32 in the tab be as large as possible, consistent with strength and the overall small size of the tab, so that a person's forefinger and thumb can protrude slightly into the opening when the tab is being gripped. The maximum width of the hole in the preferred form of the invention is about 5 mm and the maximum height is about 3 mm.

The adhesive 12 securing the tab to the veneer is preferably a hot-melt glue which is available in rod form and is electrically heated by a conventional glue gun. The glue is a thermoplastic material which is solid at room temperature but will soften and become molten as it is heated. The material is quite sticky when heated and will remain attached to the placement tab and the veneer as it solidifies. When solidified, the glue provides a strong attachment, but at the same time, it is slightly resilient so that it is comfortable to grip and provides a good "feel" for positioning purposes.

An adhesive which is currently preferred is marketed by H. B. Fuller Company, located at 1200 Walters Boulevard, Vadnais Heights, Mn. 55110. It is identified by that company as 9081-X. The exact composition of the adhesive is proprietary to that company, but it is understood that the primary component of the adhesive is ethylene vinyl acetate. Other adhesives with suitable characteristics are also probably available. Any suitable commercial glue gun is satisfactory. The adhesive may also be heated by the flame of a bunsen burner, alcohol torch or other means; however, an electrically heated adhesive dispenser is believed to be most convenient.

In utilizing the positioning tab of the invention, the restoration to be attached is initially typically mounted on a tooth model. A quantity of heated adhesive may be smeared onto the outer surface of the veneer. A quantity is also positioned on the lower edge of the placement tab. The lower edge of the tab is then immediately positioned against the veneer and the tab held there as the adhesive solidifies. This only takes a few seconds. Preferably, the adhesive is spread over the major area of the restoration, perhaps as much as 75% of the surface of a front tooth veneer. This provides a relatively large attachment base to securely attach the tab to the veneer. The adhesive, being on both sides of the tab, readily makes a strong attachment to the tab.

Figure 7:
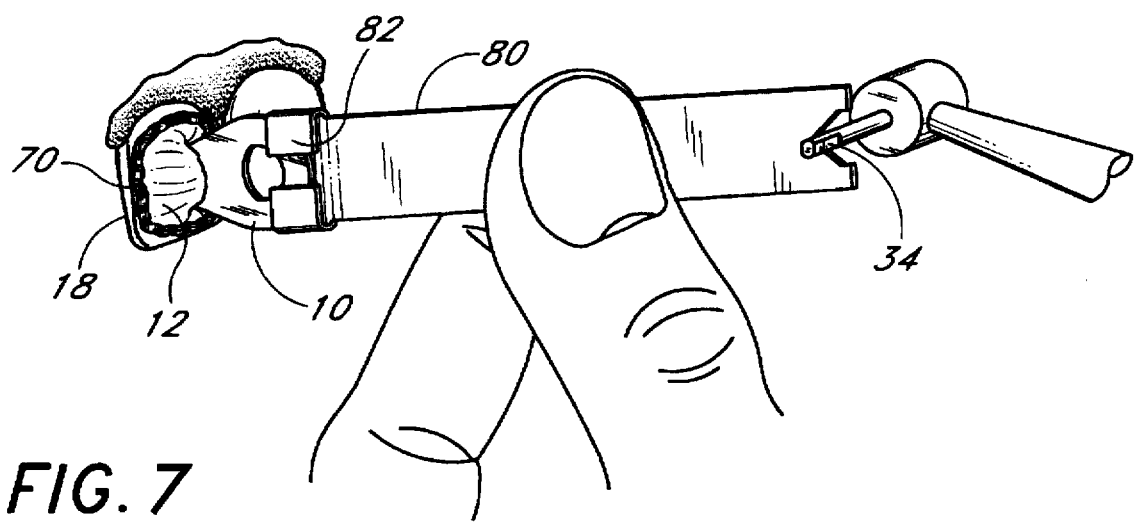
FIG. 7 is an enlarged perspective view illustrating a tab joined to the outer surface of a tooth veneer with a primer coating between the veneer and an adhesive joining the tab to the veneer and illustrating a vibration transfer tool utilized in attaching a veneer to a tooth.

While the preferred adhesive referred to above seems quite satisfactory for joining the tab to a dental restoration, if the restoration has crevasses or irregularities to facilitate bonding of the thin edge of the tab to the restoration. However, in the case of a veneer having a relatively smooth exterior surface, it is preferable that a primer coating be applied to the veneer to facilitate the joining of the adhesive to the veneer. A material which has been found to be suitable for this purpose is available from Scientific Pharmaceuticals, Inc. of 3221 Producer Way, Pomona, Calif. 91768, with the product being identified as Copal Varnish, IF-2269. The material is normally transparent and somewhat difficult to see on a tooth colored veneer. Thus in accordance with another aspect to the invention, a suitable pigment is added to the primer to make it more readily visible so that the person applying the adhesive to the veneer can see that a primer coating has been applied to the area to which the adhesive is to be applied. In a preferred arrangement, a pigment added to the varnish is identified as pylakrome bright blue LX-6258 and marketed by Pylam Products Company Incorporated, 1001 Stewart Avenue, Garden City, N.Y. 11530. With the use of this colored varnish, a thin coating 70 is applied to the veneer so it may be readily seen, as indicated in FIG. 7.

The primer may be applied to the exterior surface of a veneer in various ways, but care must be taken not to apply the primer or the adhesive to the margins of a veneer. Also, due to the relatively small size of the veneer and the small quantity of primer to be applied, as well as the need for sterility, some special techniques are useful. A sterile quantity of small sponges may be kept in a small container having an access slot in a cap. The cap may be rotated to expose one sponge in a cap slot. The sponge may then be picked up with a pair of fine pointed, angled, locking, cotton pliers from the slot in the container cap. After proper positioning of the sponge between the beaks of the pliers, the pliers may be locked to hold the sponge. A drop of the primer may be placed into a small cup of a tray, and the sponge being held by the pliers dipped into the primer. The primer then may be painted on the desired area of the labial surface of the veneer, making sure that the primer does not touch the margins of the veneer. After waiting a few seconds for the primer to dry, the adhesive may be applied to the primer coated surface.

The two points 20 on the lower edge 22 of the tab of course engage the restoration surface and provide a solid base for the attachment. The adhesive 12 flows around those points and into the holes 25, as well as into the recess 24 between the points, as shown in FIG. 1. A major advantage of the point arrangement is that it will conform to various curved exteriors of the restoration. The tab should be positioned so it extends outwardly substantially perpendicular to the surface of the restoration so that it can be conveniently gripped. While the tab can be rotationally oriented in any desired position on the restoration, it has been found that the most convenient arrangement is to position the tab so that its plane is either parallel or perpendicular with respect to a vertical axis 13 of the veneer. With larger veneers, the perpendicular orientation is usually preferable and with smaller veneers, the parallel orientation may be preferred.

After the tab has been solidly attached to the veneer, the veneer can of course be positioned on the tooth or tooth model as many times as desired or as is necessary in the various adjusting and tooth bonding steps as needed. The restoration can also be positioned on and off the dental cast in the laboratory. The restoration can also be held by the tab while the restoration is being adjusted with dental tools by either the technician or the dentist.

Figure 4:
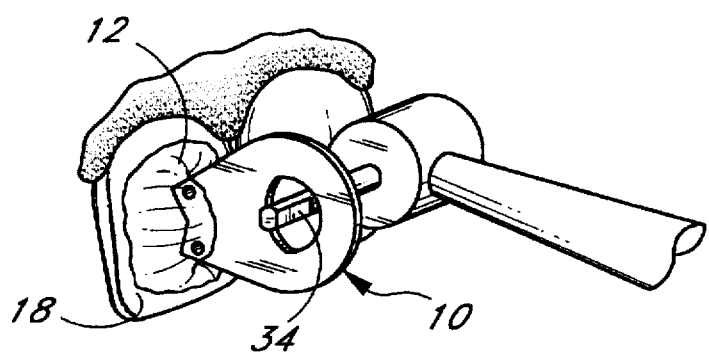
FIG. 4 is a view similar to FIG. 1 but with the tab gripped and positioned adjacent the tooth to which it is to be mounted.

As noted above, it is desirable to evenly distribute tooth bonding agent between the veneer and the tooth to be laminated. With relatively thick bonding agent it is sometimes difficult to accomplish the distribution and to extrude excess bonding agent from beneath the veneer. One example of a material being used is a composite resin sold under the trademark Herculite. In accordance with another aspect of the invention, a small shaft 34 mounted in a dental handpiece is inserted through the hole 32 in the tab and the side of the shaft is pressed against the hole edge 32b toward the tooth. As seen from FIG. 4, the shaft has a somewhat rectangular cross section, or other non-circular cross section, with the result that when the handpiece is activated, the rotation of the shaft creates a vibrating force which is transmitted into the plane of the tab and directed towards the veneer. This causes the veneer to vibrate and evenly spread the bonding material between the tooth and the restoration and helps seat the veneer in the proper position. It should be noted that the solidified adhesive that attaches the tab to the restoration is somewhat resilient, and it distributes the vibrating force applied to the restoration so that the vibrations do not damage the delicate restoration. The vibrating tool could instead be held against the outer tab edge 28. The dentist holds the tab when it is being vibrated, but for convenience the dentist's fingers are not shown in FIG. 4.

A preferred alternate arrangement for vibrating the restoration is illustrated in FIG. 7. Shown is a vibration transfer or extension tool 80 which is a stiff flat element preferably made of stainless steel. While the tool can be of various lengths, it is preferably about 1⅝ inches (42 mm) and about 5/16 inch (8 mm). Preferably the material is about 0.50–0.60 inches thick (1.2–1.5 mm). One end of the tool has flaps that have been folded over to create a partially closed loop 82 having a generally rectangular cross-section with rounded ends, as may be seen in FIG. 7. The other end of the tool has a centrally located generally V-shaped notch 84 with a mouth of about 0.14 inches (3.5 mm) and a depth of about 0.11 inches (2.7 mm). The notch is adapted to receive a shaft of the type shown in FIG. 4 at 34. As seen, the loop 82 is adapted to fit over the rounded end of a tab 10. The length of the loop is smaller than the width of the tab so that the loop only fits partially onto the tab. In use, the vibrating tool is then positioned in the notch 84 to vibrate the tab sufficiently to evenly spread the bonding material between the tooth and the veneer.

After the vibrating step is completed, the tab can then be once more gripped with the fingers so that the veneer is held stationary and pressed against the tooth 18 until the bonding agent has bonded the veneer to the tooth. The bonding agent that is typically employed for bonding the veneer to the tooth is a light-sensitive agent that will cure when irradiated with a small intense light source. The light source will pass through the thin veneer. Also, the adhesive 12 attaching the tab to the veneer is transparent enough so that the light can pass through it as well.

Figure 5:
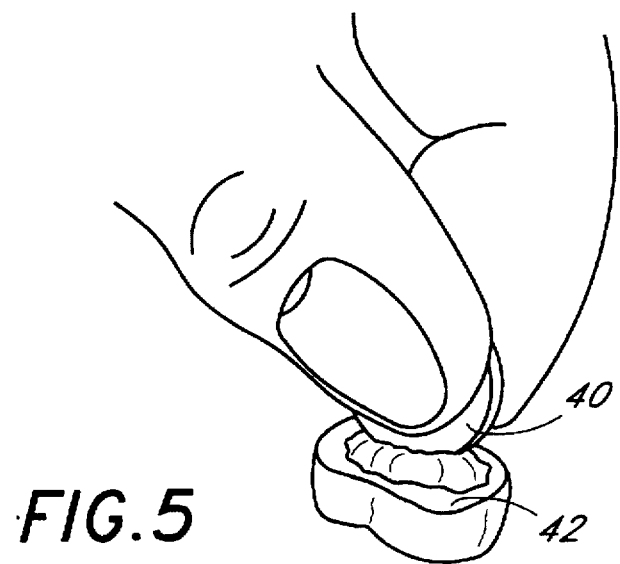
FIG. 5 is a perspective view illustrating an earlier form of a tab of the invention attached to the upper surface of a tooth crown.

The holder tab 10 may be used to position other restorations, such as dental crowns. Also, shapes other than that of the tab 10 may be utilized. Such use is schematically shown in FIG. 5, wherein the edge of a disc-shaped tab 40 is glued to the biting surface of a crown 42. The tab may be formed of glue, being sliced from a glue gun rod. In use, one curved edge is softened by heat, and pressed against the crown. The two point contact of FIG. 1 is preferable over the disc shape, but the disc is shown to illustrate that other generally thin flat shapes may be used. Of course the element 40 may be made of other materials, and glued to the crown in the manner described for the tab in connection with FIGS. 1 and 4.

The veneer is at this stage securely bonded to the tooth so that the tab and the adhesive holding it can be removed from the veneer without damaging the veneer or the tooth. A small dental knife is used to cut the adhesive between the tab and the veneer to separate the tab from the veneer. The tab and the adhesive is then discarded. The residual primer can be removed from the veneer with isopropyl alcohol or a rotary tooth cleaning cup.

Because the tabs 10 are such small elements, it is convenient to have them mounted in a vertical position with the finger gripping area extending upwardly so as to facilitate gripping between the thumb and forefinger of a operator's hand. Further, it is desirable that a tab be gripped in a position to be attached to a veneer and positioned on a patient without regripping. FIG. 5 illustrates such an arrangement wherein a flat elongated rectangular or oblong, support 50 is shown having a row of slots 52 formed in its upper surface 50a. Each slot 52 is adapted to receive the lower end of one of the tabs 10. As seen, the support 50 has an elongated front wall 50b spaced from an elongated rear wall 50c and joined by short end or edge walls 50d and 50e. Further, each slot 52 has a generally rectangular cross-section with a front edge 52a and a rear edge 52b closely spaced from and parallel to the front and rear support walls 50b and 50c. The front and rear edges 52a and 52b of each slot are joined by short side edges 52c. As can be seen, the slots 52 are positioned and spaced in a side-edge-to-side-edge arrangement, with the slots being aligned in a row defined by the longer front and rear edges 52a and 52b of the slots.

The slots extend from the upper surface 50a of the support completely through the support, opening to a lower wall 50f.

The upper end of each slot 52 is larger than the lower end. The slots are dimensioned so that when the lower end of a tab is positioned in a slot the side edges 26 on the lower end of the tab 10 engage the side edges 52c of the slot. The front to rear dimension of a slot is only slightly greater than the thickness of the tab, with the result that the tab is captured in the vertical position illustrated in FIG. 5. As seen, the front and rear surfaces of the tab are generally parallel to the front and rear walls of the support. The side edges 52c of the slots 52 taper gradually from the upper end to the lower end. Such taper is similar to the tapered edges 26 of the tabs 10. Thus the lower end of the tab nests in a slot 52 for easy insertion and removal from the slot. In one form of the invention, the side edges 52c taper at an angle of about 22° and the upper end is about 0.3 inch in width between the side edges 52c. The upper ends of adjacent slots are spaced a little more than 0.2 inch.

The support 10 is desirably less than ½ inch thick, and preferably is only about a ¼ of an inch. Further, the front to rear dimension of the support is only about one inch, with the slots being centrally positioned between the front and rear walls. With this arrangement, the dentist or assistant may conveniently grip a tab 10 in its gripping area 30 with a thumb 60 and forefinger 62 while the middle finger 64 or ring finger 66 extends adjacent the rear wall of the support and downwardly onto the surface on which the support rests. This provides a stabilizing action for the operator's hand while gripping a small tab, as may be seen from FIG. 5.

It should be noted that the operator's fingers are gripping the tab from above which is the same position the operator's hand is typically oriented when the tab is attached to a veneer that is being positioned on a patient's tooth. Thus, with the tab 10 so positioned, the operator can conveniently lift it from the support and hold it while the lower edge of the tab is dipped in the adhesive and attached to a veneer. Typically the veneer is positioned on a dental cast adjacent the tab support. A finger from the operator's other hand is usually positioned behind the tooth on the dental cast on which the veneer has been positioned to support the veneer. The veneer may then be lifted by the tab and positioned on the patient's tooth or laboratory model, without the operator having to release the tab until the veneer has been positioned on the patient's tooth. Thus the arrangement illustrated and described increases the efficiency of the operation and minimizes the risk of a veneer or a tab being dropped. By having a row of tabs supported in a row of slots, the operator can conveniently place a series of veneers on a patient's teeth or lab model.

Figure 6:
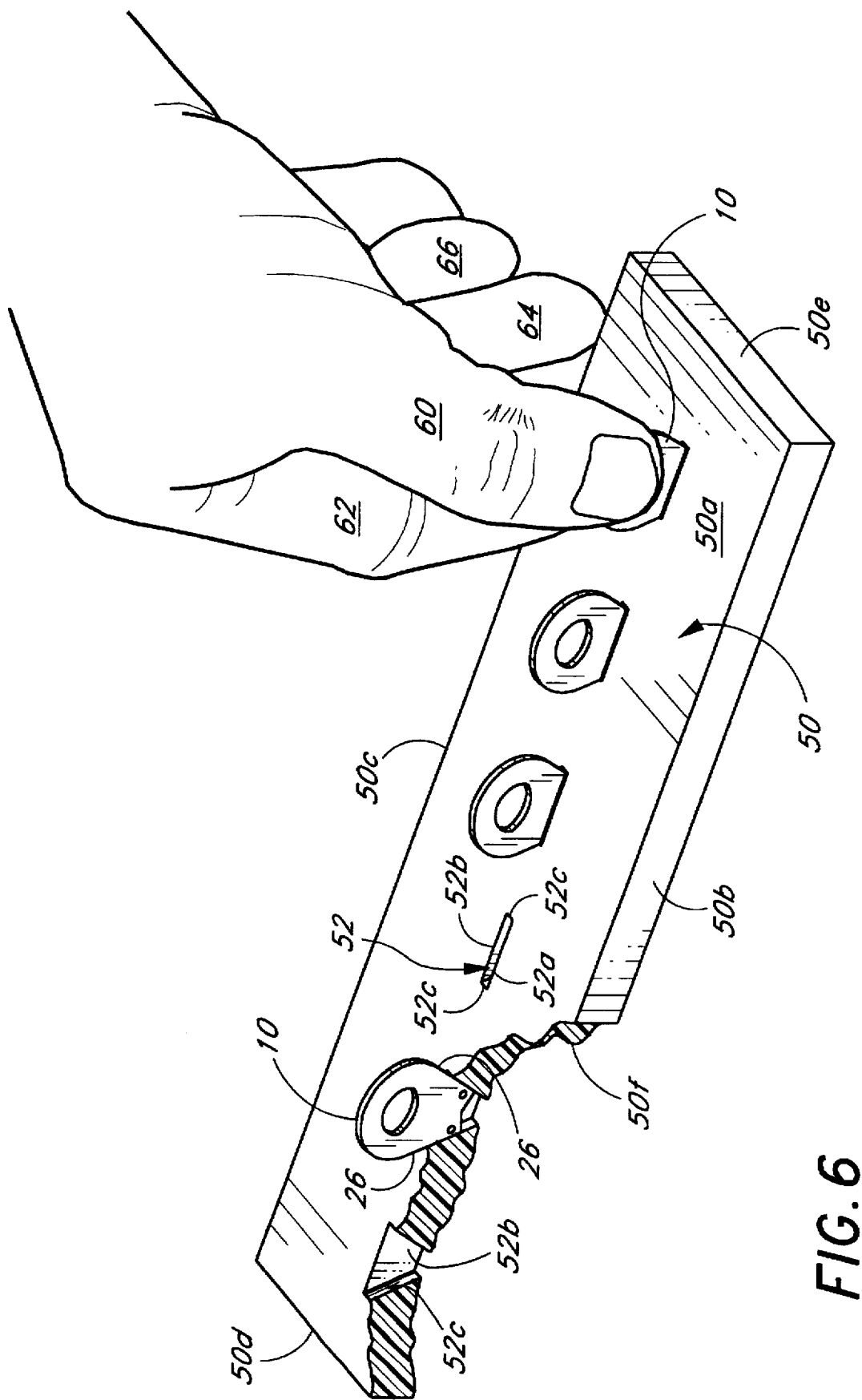
FIG. 6 is a perspective view illustrating a group of tabs positioned in a tab support.
Figure 8:
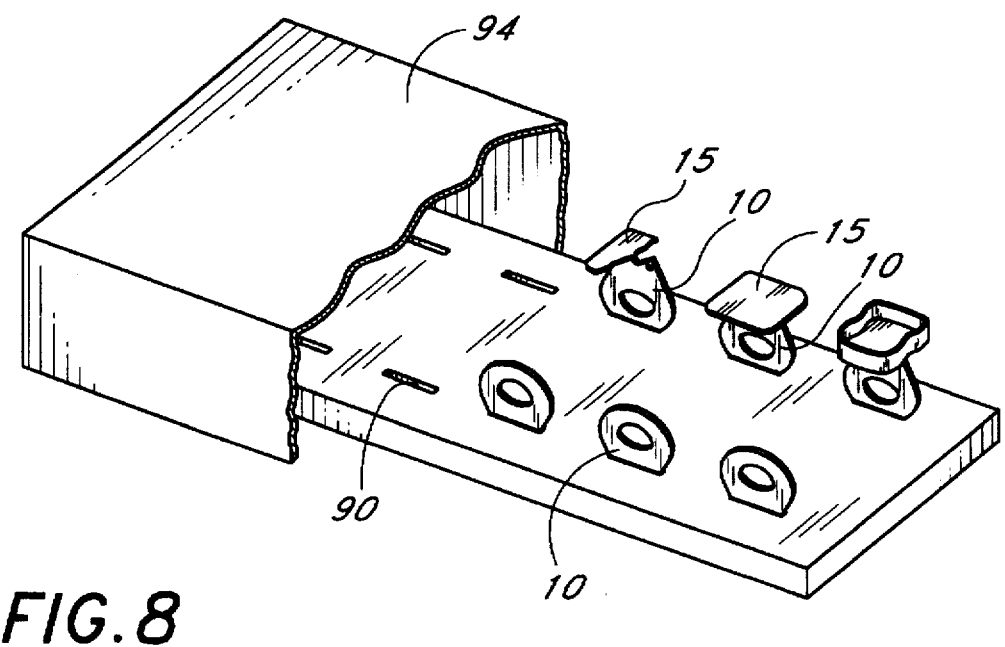
FIG. 8 is a perspective, partially cut-away view illustrating tabs positioned in another embodiment of a tab support.

While the support illustrated in FIG. 6 is convenient for positioning a group of tabs when a group of veneers are to be installed on the particular patient, a preferred embodiment of another holder is illustrated in FIG. 8. That holder has two rows of six slots 90 in spaced edge to edge relation. They are similar to those shown in FIG. 6 except that they are wider than the tabs, preferably about 0.4 inches (10 mm), and need not have tapered sides. In this holder there is a thin bottom to prevent the tab from falling through the support. As a variation of this, one row of the holder could have slots as in FIG. 6 for receiving the pointed ends of the tab, and a second row could have the wider slots of FIG. 9 to receive the rounded ends of the tabs.

In use, it is contemplated that a group of tabs be positioned in one row of slots as shown in FIG. 9. A tab is then gripped and attached to a veneer as described above. The tab with the veneer attached is then repositioned in the holder with the rounded end of the tab being inserted into one of the slots with the attached veneer extending upwardly, as shown in the drawing. This process is repeated until all of the veneers to be mounted on the patient's teeth are positioned in the holder with the veneers facing upwardly. Bonding material may then be conveniently applied to the upwardly facing surfaces of each of the veneers. An amber-colored transparent cover 94 is then positioned over the holder and the tabs to prevent certain light rays from prematurely curing the bonding material. The veneers then may be attached to the patient's teeth one by one, in the manner described above. The cover is removed to withdraw one tab with its attached veneer, and the cover is then replaced to prevent curing of the bonding material on the other veneers while the withdrawn veneer is being attached to a tooth.

While the tab system has been described in a manner primarily emphasizing the use of the tabs by the dentist in installing veneers, the tabs, as noted above, are also useful with other dental restorations. In addition to positioning restorations on the patient, the system is very useful in the laboratory where the restorations are being fabricated. Typically, the restorations must be handled a number of times in fabricating and inspecting them, and the tabs are convenient for holding the restorations during such operations. Also the primer can be used with small restorations such as inlays to enhance the adhesive quality of hot-melt glue to the surface of restorations when other types of restoration placement tools are used other than the tab type.

What is claimed is:

1. A method of mounting a dental restoration to a tooth to be restored comprising:

applying to an exterior surface of said restoration a primer that will facilitate the adhesion of an adhesive to the exterior surface of the restoration, said primer being removable from the restoration with isopropyl alcohol; and attaching a restoration placement tool to the primer coated exterior of the restoration by applying hot-melt adhesive to said primer coated surface.

2. The method of claim 1, including gripping the tool at one end and dipping the other end of the tool into an adhesive and pressing the dipped end onto the restoration.

3. A method of mounting a dental restoration to a tooth to be restored comprising:

applying to an exterior surface of said restoration a primer that will facilitate the adhesion of adhesive to the exterior surface of the restoration;

attaching the restoration placement tool to the primer coated exterior surface of the restoration; and positioning one or more tools in slots in a holder;

gripping one tool and attaching one edge of the one tool to an exterior surface of a dental restoration utilizing an adhesive;

and inserting the one tool into a slot on said holder with the restoration extending upwardly.

4. The method of claim 3, including applying a tooth bonding agent to the upturned surface of the restoration.

5. A method of mounting a dental restoration to a tooth to be restored comprising:

applying to an exterior surface of said restoration a primer that will facilitate the adhesion of an adhesive to the exterior surface of the restoration;

positioning one end of a restoration placement tool in a holder;

removing said tool by gripping an opposite end of the tool;

attaching the tool to said dental restoration; and repositioning said opposite end of the tool in the holder with the restoration attached.

6. The method of claim 5, including applying a tooth bonding agent to the restoration and covering the holder and the restoration with a cover which blocks light to prevent curing of the tooth bonding agent.

7. A method of mounting a dental restoration to a tooth to be restored comprising:

applying to an exterior surface of said restoration a primer that will facilitate the adhesion of an adhesive to the exterior surface of the restoration, said primer having pigment added to it to make it more visible when applied to a dental restoration; and attaching a restoration placement tool to the primer coated exterior surface of the restoration.

8. A method of mounting a series of dental restorations to a series of teeth to be restored, comprising:

positioning one end of each of a series of tabs into a series of slots in a holder, with opposite ends of the tabs extending upwardly for easy gripping between a persons thumb and forefinger;

selecting a tab and removing it from the holder and applying it to the exterior surface of a dental restoration utilizing a suitable adhesive; and returning the selected tab to a slot in the holder with the restoration positioned above the slot.

9. The method of claim 8, including attaching a series of said tabs to a series of dental restorations and returning the tabs to slots in the holder with the dental restorations extending upwardly, applying light sensitive tooth bonding agent to the upwardly facing surfaces of the dental restorations, and positioning a cover over the holder and the dental restorations being supported by the holder so as to prevent light curing of the adhesive.

10. A dental combination, comprising:

a dental restoration;

a primer applied to an exterior surface of the restoration of a type which will facilitate the adhesion of an adhesive to the restoration, said primer having colored pigment in it so that the primer is easily visible on the dental restoration;

an adhesive applied to the primer coated surface on the restoration; and a restoration placement tool having an end position in the adhesive with the tool extending away from the exterior surface of the restoration.

11. A dental combination, comprising:

a thin, flat, disk-like element to be attached on one edge to a dental restoration, with the remainder of the element extending away from the restoration to form a tab with an end to be gripped between a thumb and a forefinger; and a vibration transfer tool having one end which fits over said tab end and engages edges of said element spaced from said one edge and said tool having an opposite end formed to receive a vibrator so that vibration from the vibrator is transferred through the tool and edgewise through the tab for purposes of assisting the spreading of bonding agent between the dental restoration and a person's tooth.

12. A method of positioning a dental restoration on a tooth or tooth model, comprising:

attaching with an adhesive an edge of a generally thin, flat element to an exterior surface of the restoration, with the element extending generally perpendicular to said exterior surface of the restoration to form a finger-gripping tab;

gripping said tab between the thumb and finger of one hand close to the restoration so as to facilitate adjusting or positioning of the restoration on a tooth or tooth model;

applying a tooth bonding material to said restoration;

placing the restoration on said tooth; and positioning a vibrating tool against an edge of said tab to vibrate said restoration against said bonding material.

* * * * *